United States Patent

Bigatti et al.

Patent Number: 5,945,518
Date of Patent: Aug. 31, 1999

[54] PROCESS FOR THE PREPARATION OF ANTHRACYCLINE ANTIBIOTICS

[75] Inventors: Ettore Bigatti, Rho; Francesco Bianchi, Milan, both of Italy

[73] Assignee: Sicor Societa' Italiana Corticosteroida S.p.A., Milan, Italy

[21] Appl. No.: 08/913,783

[22] PCT Filed: Mar. 19, 1996

[86] PCT No.: PCT/EP96/01174

§ 371 Date: Sep. 18, 1997

§ 102(e) Date: Sep. 18, 1997

[87] PCT Pub. No.: WO96/29335

PCT Pub. Date: Sep. 26, 1996

[30] Foreign Application Priority Data

Mar. 22, 1995 [IT] Italy ................................ MI95A0566

[51] Int. Cl.⁶ .......................... C07C 49/423; C07H 17/08
[52] U.S. Cl. ............................................. 536/6.5; 552/201
[58] Field of Search ................ 552/201; 536/6.5

[56] References Cited

U.S. PATENT DOCUMENTS

| | | | |
|---|---|---|---|
| 4,537,882 | 8/1985 | Horton et al. | 552/201 |
| 4,749,693 | 6/1988 | Angelucci et al. | 552/201 |
| 5,015,745 | 5/1991 | De Bernardinis et al. | 552/201 |
| 5,037,970 | 8/1991 | Angelucci et al. | 552/201 |

Primary Examiner—John Kight
Assistant Examiner—Raymond Covington
Attorney, Agent, or Firm—Bucknam and Archer

[57] ABSTRACT

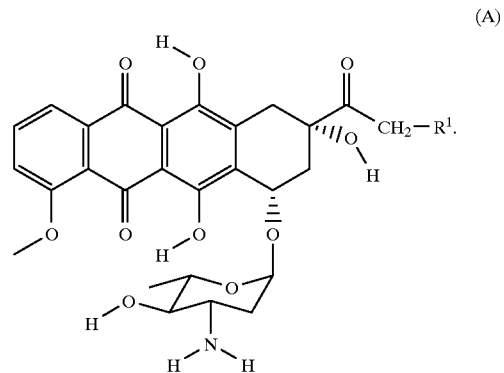

A process for the preparation of antibiotics of the anthracycline class of formula (A), wherein $R^1$ is hydrogen, OH, or $OCOR^2$, wherein $R^2$ is a $C_1$–$C_4$-alkyl group; which comprises the epimerization of the 4' hydroxy group of the daunosamine residue by nucleophilic substitution of a triflate group with a carboxylate, which epimerization is carried out on the whole molecule with the hydroxy groups being protected, and subsequent transformation into the final product.

26 Claims, No Drawings

PROCESS FOR THE PREPARATION OF ANTHRACYCLINE ANTIBIOTICS

The present invention relates to a process for the preparation of anthracycline antibiotics.

FIELD OF THE INVENTION

Epirubicin (epidoxorubicin) and epidaunomycin are antibiotics belonging to the anthracycline class having antitumoral activity.

These compounds differ from the antitumorals doxorubicin and daunorubicin in the configuration of the hydroxy group at the C-4' position of the glycosidic moiety of the molecule, which configuration is respectively axial in doxo- and daunorubicin and equatorial in epirubicin and epidaunorubicin.

BACKGROUND OF THE PRIOR ART

Doxorubicin has been used for a long time in the antineoplastic treatment, for a review see Arcamone, ed. "Doxorubicin", Acad. Press, New York 1981. A serious side-effect of doxorubicin is the onset of often irreversible myocardiopathies.

Epirubicin was found to have advantageous pharmacological properties compared with its analogue, showing an equivalent antitumoral activity but less side-effects (R. B. Weiss et al., Cancer Chemother. Pharmacol. 18, 185–97 (1986)).

The starting synthesis of epirubicin involved the condensation between daunorubicin aglycone of formula (B)

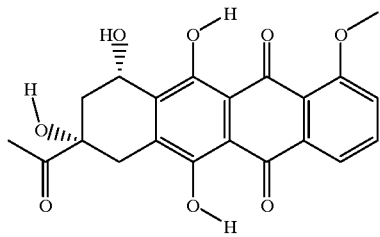

(B)

and the 1-chloro-derivative of acosamine protected as trifluoroacetamide (Arcamone, F. et al., J. Med. Chem., 18, 7, 703–707, (1975)), subsequent deprotection and working up of the side chain with a method well known in literature, already used for the transformation of daunorubicin into doxorubicin (E. M. Acton, J. Med. Chem., 17,65 (1974); DE 1917874).

Trifluoroacetylacosaminyl chloride N,O derivative was obtained by synthetic transformation of various natural sugars with a number of rather complex, expensive processes.

Italian Patent 1,163,001 and, subsequently, G. Bonadonna in "Advances in Anthracycline Chemotherapy Epirubicin", Masson Ed., Milan, Italy, 1984, disclose a synthesis process carried out on the whole N-trifluoroacetyldaunorubicin glycoside. This process comprises the oxidation of the hydroxy group at C-4' to keto group, then its stereoselective reduction to hydroxy group by means of sodium borohydride. The oxidation reaction has to be performed at exceedingly low temperatures (−70° C.). The keto derivative is very delicate and unstable. Moreover, the reduction with sodium borohydride must be carried out at a low temperature to minimize the competitive reduction of the aglycone carbonyl group.

Although not stated, the maximum isomerization yields which can deduced from said patent are of about 48%.

Another method for the epimerization of C-4' is described by B. Barbieri et al. Cancer Research, 47, 4001 (1987). This method aims at obtaining 4'-halogen-daunorubicin, then effects the epimerization from the equatorial configuration to the axial one, i.e. in a direction opposite to that desired in the present invention. The epimerization reaction is carried out by nucleophilic substitution of the triflate group (equatorial) with a tetrabutylammonium halide.

SUMMARY OF THE INVENTION

Now a novel method has been found for the isomerization of the 4' hydroxy group of the daunosamine residue on the whole anthracycline antibiotic molecule, reaction conditions which can be regulated more easily, particularly with respect to the reaction temperature, and with easier purification procedures.

According to this method, the epimerization of the 4' hydroxy group from the axial configuration to the equatorial one of the daunosamine residue, which is suitably protected at the amino group, is obtained by introducing a strong leaving group and subsequently substituting it with a carboxylate group, with inversion of the configuration of the 4' carbon atom, subsequently hydrolysing the carboxylic ester, restoring the hydroxy group, removing the amino-protective group.

During the study of the epimerization reaction, the yields in the desired epimer were found to be not very high, due to a side product formed in competition with the substitution reaction of the triflate leaving group.

Surprisingly, the protection of the hydroxy groups of the aglycone moiety, particularly that at the 9 position, made it possible to obtain the desired epimer without competitive formation of the side product.

For the purposes of the process according to the invention, it is essential that the hydroxy group at the 9 position of the aglycone moiety is protected. The protection of the hydroxy groups at the 6 and 11 positions can improve the yields.

Therefore, it is an object of the present invention process for the preparation of antibiotics of the anthracycline class of formula (A)

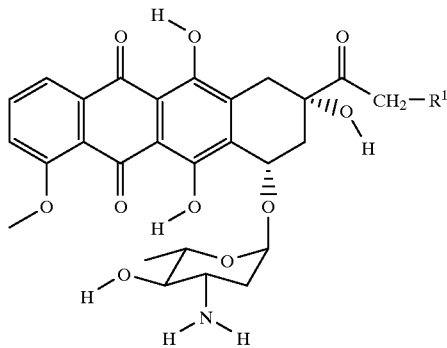

(A)

wherein $R^1$ is hydrogen, OH, or $OCOR^2$, in which $R^2$ is a $C_1$–$C_4$-alkyl group, which comprises the epimerization of the 4' hydroxy group by means of nucleophilic substitution of the 4' triflate group with a carboxylate group, upon protection of the hydroxy groups of the aglycone moiety of the molecule.

DETAILED DISCLOSURE OF THE INVENTION

According to a first embodiment of the invention, the preparation process comprises:

a) reaction of N-protected daunorubicin of formula (I)

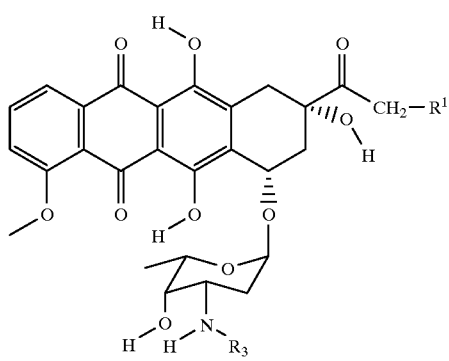

(I)

or a derivative thereof,
wherein $R^1$ is hydrogen, halogen, suitably protected hydroxy; $R_3$ is an amino-protective group;
with triflic acid or a reactive derivative thereof, to give the compound of formula (II)

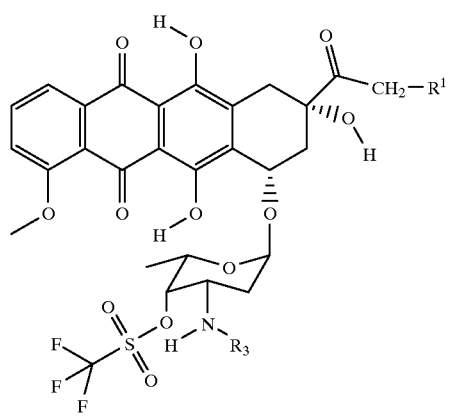

(II)

wherein $R^1$ and $R_3$ are as defined above;

b) protection of the hydroxy group at the 9 position, and optionally those at 6 and 11, to give the intermediate of formula (III)

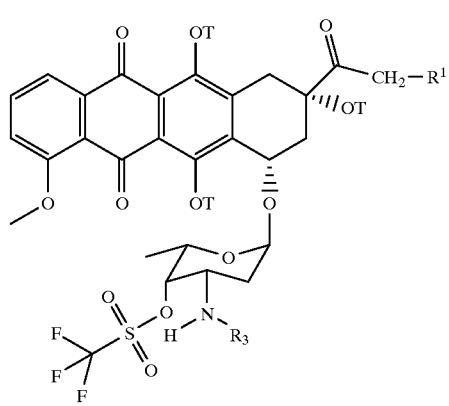

(III)

wherein T is a protective group, $R^1$ and $R^3$ are as defined above;

c) treatment of the compound obtained in step b) with a salt of a secondary or tertiary amine with a carboxylic acid of formula RCOOH, wherein R is an aliphatic residue, optionally substituted or interrupted by heteroatoms, or an optionally substituted aromatic residue, to give the ester of formula (IV)

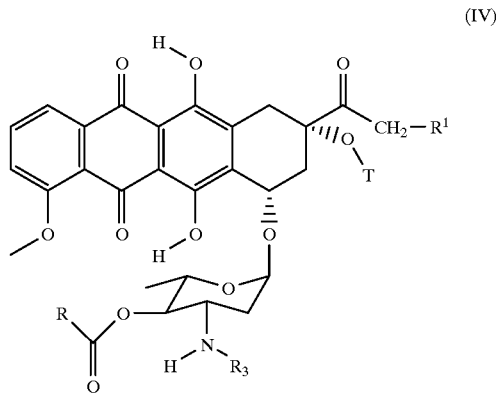

(IV)

wherein R, $R_1$, $R_3$ and T are as defined above;

d) deprotection of the hydroxy group at the 9 position, to give the intermediate of formula (V)

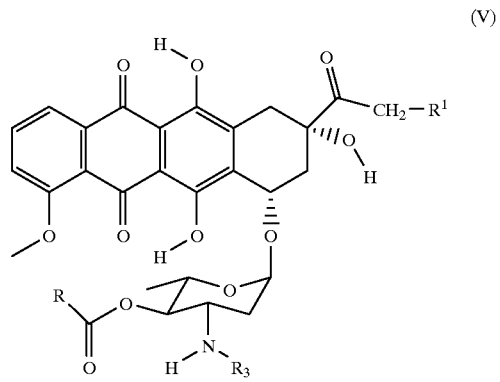

(V)

wherein R, $R_1$ and $R_3$ are as defined above;

e) hydrolysis of the ester to give N-protected epidaunorubicin of formula (VI)

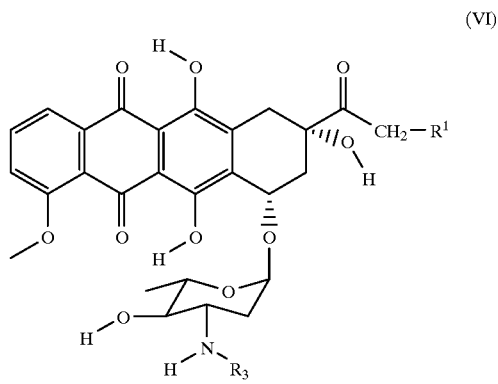

(VI)

wherein $R^1$ and $R_3$ are as defined above;

f) removal of the amino-protective group and, if desired, g) transformation into epirubicin or an ester thereof of formula (A)

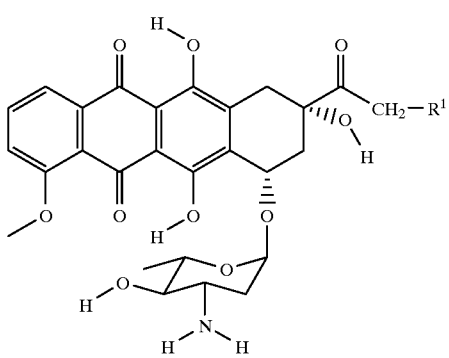

(A)

wherein $R^1$ is OH or $OCOR^2$, in which $R^2$ is as defined above.

The starting compound is preferably daunorubicin trifluoroacetamide, or a derivative thereof, known in the art and anyhow preparable according to known methods starting from daunorubicin and trifluoroacetic anhydride (e.g. J. Med. Chem., 18, 7, 703–707, (1975)).

Other amino-protective groups can be used as well, e.g. carbamate esters such as fluorenylmethoxy carbamate (Fmoc) and the like.

As the leaving group, the triflate (trifluoromethylsulfonic) ion is used herein, which is commercially available and can be used in the form of the corresponding anhydride. The reaction is carried out in a suitable solvent which does not affect the reactants and the final product, such as poorly polar aprotic solvents, for example dichloromethane, dicloroethane, chloroform, dioxane, tetrahydrofuran, benzene.

The reaction is carried out at a low temperature (about 0° C.) for a time sufficient to complete it.

The resulting intermediate compound of formula (II) can be used directly in the subsequent step, without recovering it. After that, in the same reaction vessel the suitable reagent is added, which provides the protective group for the hydroxy groups at the 9 position and, if desired, at 6 and 11, of the aglycone moiety. This intermediate (III) can also be directly used in the subsequent step. Suitable protective groups in this reaction are known to those skilled in the art. The trimethylsilyl group is preferred due to its low commercial cost, but other silyl derivating groups are equally valid.

In the subsequent step the carboxylate is added in the form of a salt with a secondary or tertiary amine. The reaction was found to proceed unsatisfactorily with ammonium quaternary salts.

Examples of carboxylates are formate, acetate, isobutyrate, trimethylsilylacetate, p-nitrobenzoate, haloacetates, such as trifluoroacetate. Any substituent groups of the aliphatic or aromatic residue or any heteroatoms in the aliphatic chain of the RCOOH acid should not interfere with the nucleophilic substitution reaction. A preferred amine is triethylamine. The reaction is carried out at a temperature ranging from 0° to 50° C., preferably at room temperature, for a time sufficient to complete it. At the end, the product of formula (IV) is recovered according to conventional procedures, then it is suitably treated with a conventional procedure to deprotect the hydroxy group at 9, thereby obtaining the compound of formula (V).

The hydrolysis of the ester is carried out in alkaline conditions as it is well known to those skilled in the art, for example dissolving compound (V) in a polar solvent, such as methanol, and treating it with an alkali or alkaline-earth metal hydroxide, such as sodium hydroxide. N-Protected epidaunorubicin (VI) is thereby obtained and after hydrolysis of the protective group on the nitrogen, the epidaunorubicin (A; $R^1$=H) is obtained which, if desired, is transformed into epirubicin or an ester thereof (A; $R^1$=OH or $OCOR^2$) with processes known in the art (e.g. A. Suarato et al. Carbohydrate Res., 98, c1–c3 (1981)).

According to another embodiment of the present invention, epirubicin is prepared starting from doxorubicin of formula (C),

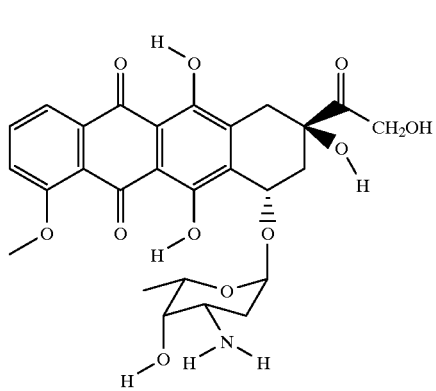

(C)

said process comprising:

a) reaction of doxorubicin with a suitable protective agent for the hydroxy groups at 9 and 14, and subsequent protection of the 3' amine, to give the compound of formula (VII)

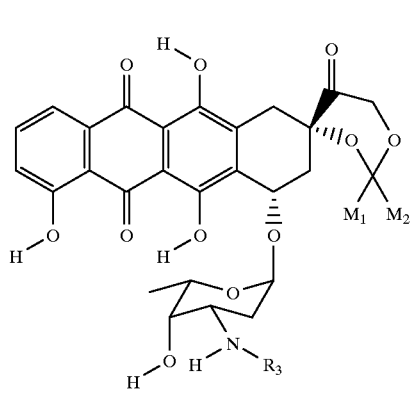

(VII)

wherein $M_1$ is a $C_1$–$C_4$-alkoxy group and $M_2$ is hydrogen or a $C_1$–$C_4$-alkyl group;

b) reaction of the intermediate (VII) with triflic acid or a reactive derivative thereof, to give the compound of formula (VIII)

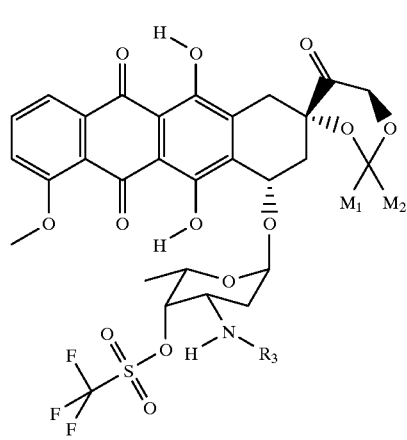

(VIII)

wherein $M_1$, $M_2$ and $R_3$ are as defined above;

c) protection of the hydroxy groups at 6, 11, to give the intermediate of formula (IX)

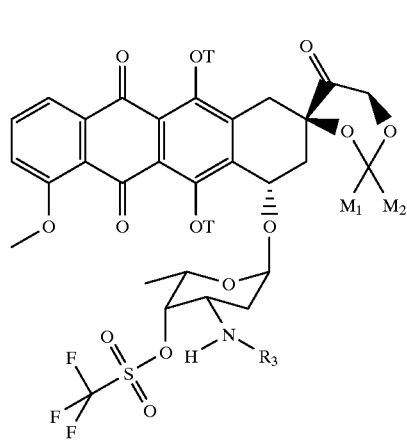

(IX)

wherein T is a protective group, $M_1$, $M_2$ and $M_3$ are as defined above;

d) treatment of the compound obtained in step c) with a salt with a secondary or tertiary amine with a carboxylic acid of formula RCOOH, wherein R is an aliphatic residue optionally substituted or interrupted by heteroatoms; an optionally substituted aromatic residue, to give the ester of formula (X)

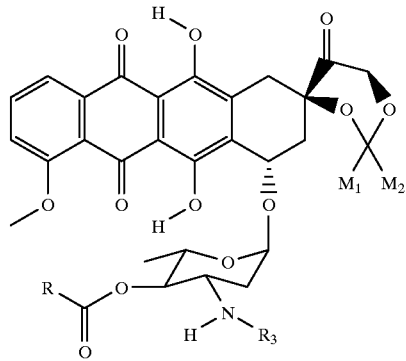

(X)

wherein R, $R_3$, $M_1$ and $M_2$ are as defined above;

e) hydrolysis of the ester and subsequent removal of the protective group of the hydroxyl groups at 9 and 14 and of the amino group.

The starting compound is prepared conventionally. A preferred example is the reaction of doxorubicin with triethyl orthoformate ($M_1$=$C_2H_5O$, $M_2$=H) (see Arcamone, ibid. p. 21). The subsequent steps are carried out as described for the first embodiment of the invention. In particular, step d) is effected at a temperature ranging from 0° to 50° C., preferably at room temperature. The protecting groups are removed according to well known methods.

The following examples further illustrate the invention.

Example 1

A mixture of compound I (5 g) in dichloromethane (500 ml) and pyridine (2.5 ml), cooled at 0° C., is slowly added with a solution of trifluoromethanesulfonic anhydride (2.5 ml) in dichloromethane (125 ml). The mixture is left to react for about 1 hour to form the triflate (compound II).

N,O-bis-trimethylsilylacetamide (10 ml) is added, heating at room temperature and stirring for 4 hours. The tris silylate (compound III, T=trimethylsilyl) is added with a 0.1 molar solution of triethylamine isobutyrate in dichloromethane (500 ml) and stirring at room temperature for a further 15 hours. The reaction mixture is washed with 500 ml of 0.25 N hydrochloric acid, then with a 2% solution of sodium bicarbonate and finally with 500 ml×2 of water. The organic phase is dried over sodium sulfate, filtered and evaporated to dryness.

5 g of compound IVc are obtained (R=$(CH_3)_2CH$, T=Si$(CH_3)_3$, $R_3$=$CF_3CO$).

$^1$H-NMR (CDCl$_3$): ppm: 13.92 (s, 1H, phenol OH); 13.40 (s, 1H, phenol OH); 8.05 (d, 1H, H-1); 7.80 (t, 1H, H-2); 7.40 (d, 1H, H-3) 6.55 (d, 1H, CONH); 5.37 (d, 1H, H-1'); 5.05 (m, 1H, H-7); 4.65 (t, 1H, H-4'); 4.55–4.40 (m, 2H, H-3' and H-5'); 4.08 (s, 3H, OCH$_3$); 3.25 (q, 2H, 10-CH$_2$); 2.65–2.55 (m, 1H, CHCOO); 2.45–2.20 (m, 2H, 8-CH$_2$); 2.37 (s, 3H, COCH$_3$); 2.10–1.70 (m, 2H, 2'-CH$_2$); 1.30–1.10 (m, 9H, 5'-CH$_3$ and (CH$_3$)$_2$); 0.15 (s, 9H, Si(CH$_3$)$_3$).

Example 2

Following the procedure described in Example 1, using triethylamine acetate, 5 g of compound IVa are obtained (R=CH$_3$, T=Si(CH$_3$)$_3$, R$_3$=CF$_3$CO).

Example 3

Following the procedure described in Example 1, using diethylamine formate, 5.1 g of compound IVd are obtained (R=H, T=Si(CH$_3$)$_3$, R$_3$=CF$_3$CO).

Example 4

Following the procedure described in Example 1, using triethylamine p-nitrobenzoate, 4.9 g of compound IVe are obtained (R=p-O$_2$NC$_6$H$_4$, T=Si(CH$_3$)$_3$, R$_3$=CF$_3$CO).

Example 5

Following the procedure described in Example 1, using triethylamine trimethylsilyl acetate, 5.1 g of compound IVb are obtained (R=(CH$_3$)$_3$ SiCH$_2$, T=Si(CH$_3$)$_3$, R$_3$=CF$_3$CO).

Example 6

A solution of compound IVc (5 g) in dichloromethane (1000 ml) is added with a 48% aqueous solution of potassium fluoride (20 ml) and 1 g of triethylamine acetate. The mixture is stirred at room temperature for 2 days, then the phases are separated. The organic phase, after drying over sodium sulfate, is evaporated to dryness.

The residue is purified through a column (silica gel: eluent dichloromethane-acetone 95:5) to yield 4.5 g of compound Vc (R=(CH$_3$)$_2$CH).

$^1$H-NMR (CDCl$_3$): ppm: 14.00 (s, 1H, phenol OH); 13.28 (s, 1H, phenol OH); 8.03 (d, 1H, H-1); 7.79 (t, 1H, H-2); 7.40 (d, 1H, H-3) 6.68 (d, 1H, CONH); 5.53 (d, 1H, H-1'); 5.30 (m, 1H, H-7); 4.65 (t, 1H, H-4'); 4.40–4.10 (m, 2H, H-3' and H-5'); 4.10 (s, 3H, OCH$_3$); 3.35–2.85 (m, 2H, 10-CH$_2$); 2.65–2.55 (m, 1H, CHCOO); 2.45 (s, 3H, COCH$_3$); 2.45–1.70 (m, 4H, 8-CH$_2$ and 2'-CH$_2$); 1.27 (d, 3H, 5'-CH$_3$); 1.15 (t, 6H, (CH$_3$)$_3$).

Example 7

Starting from IVa (5 g), with the same procedure as in Example 6, 4.2 g of compound Va are obtained (R=CH$_3$, R$_3$=CF$_3$CO).

Example 8

Starting from IVd (5.1 g), with the same procedure as in Example 6, 4.4 g of compound Vd are obtained (R=H, R$_3$=CF$_3$CO).

Example 9

Starting from IVe (4.9 g), with the same procedure as in Example 6, 4.3 g of compound Ve are obtained (R=p-O$_2$NC$_6$H$_4$, R$_3$=CF$_3$CO).

Example 10

Starting from IVb (5.1 g), with the same procedure as in Example 6, 3.9 g of compound Va are obtained (R=CH$_3$, R$_3$=CF$_3$CO).

Example 11

A solution of compound Vc (4.5 g) in methanol (270 ml) is treated with 0.3 ml of a 10% solution of sodium hydroxide for 2 hours. The mixture is neutralized with 0.1 ml of acetic acid and evaporated to dryness. The residue is dissolved in 20 ml of dichloromethane and 0.5 ml of water.

The solution is left to crystallize for 10 hours, to obtain 3 g of compound VI (R$^1$=H, R$_3$=CF$_3$CO).

$^1$H-NMR (CDCl$_3$): ppm: 14.00 (s, 1H, phenol OH); 13.25 (s, 1H, phenol OH); 8.05 (d, 1H, H-1); 7.80 (t, 1H, H-2); 7.40 (d, 1H, H-3) 6.55 (d, 1H, CONH); 5.55 (d, 1H, H-1'); 5.25 (m, 1H, H-7); 4.10 (s, 3H, OCH$_3$); 4.10–3.85 (m, 3H, H-3', H-4' and H-5'); 3.35–2.85 (dd, 2H, 10-CH$_2$); 3.30 (s, 1H, 9-OH); 2.40 (s, 3H, COCH$_3$); 2.40–1.75 (m, 4H, 8-CH$_2$ and 2'-CH$_2$); 1.40 (d, 3H, 5'-CH$_3$).

Example 12

Starting from Va (4.2 g), with the same procedure as described in Example 11, 3.5 g of compound VI are obtained (R$^1$=H, R$_3$=CF$_3$CO).

Example 13

Starting from Vd (4.4 g), with the same procedure as described in Example 11, 3.9 g of compound VI are obtained (R$^1$=H, R$_3$=CF$_3$CO).

Example 14

Starting from Ve (4.3 g), with the same procedure as described in Example 11, 2.9 g of compound VI are obtained (R$^1$=H, R$_3$=CF$_3$CO).

Example 15

A mixture of doxorubicin hydrochloride (1.6 g) in dimethylformamide (32 ml) is added with triethyl orthoformate (8 ml) and trifluoroacetic acid (0.8 ml). The resulting solution is stirred at room temperature for 3 hours, then diluted with dichloromethane (60 ml) and added with N-methylmorpholine (2.5 ml). After cooling at 0° C., a solution of trifluoroacetic anhydride (0.8 ml) in dichloromethane (6 ml) is added. The mixture is reacted for 3 hours at 0° C., then 3 g of sodium bicarbonate and 30 ml of methanol are added. After about 20 minutes, the reaction mixture is washed with 50 ml of water, 50 ml of 0.25 N hydrochloric acid and 50 ml of water. The organic phase is dried over sodium sulfate and evaporated to dryness.

The residue (compound VII, M$_1$=C$_2$H$_5$O, M$_2$=H) is dissolved in 100 ml of dichloromethane and 5 ml of pyridine, cooled at 0° C. and added drop by drop with a solution of trifluoromethanesulfonic anhydride (0.5 ml) in dichloromethane (20 ml). The mixture is reacted at 0° C. for about 1 hour to obtain the triflate (compound VIII M$_1$=C$_2$H$_5$O, M$_1$=H, R$_3$=CF$_3$CO).

2 ml of bis-trimethylsilylacetamide are added, warming at room temperature for 4 hours to obtain the bis silylate (compound IX, M$_1$=C$_2$H$_5$O, M$_1$=H, T=Si(CH$_3$)$_3$, R$_3$=CF$_3$CO), then a 1M solution of triethylamine formate in dichloromethane (100 ml) is added. The mixture is reacted for 15 hours to obtain compound (X) (R=H, M$_1$=C$_2$H$_5$O, M$_2$=H).

10 ml of a 48% solution of potassium fluoride and 20 ml of methanol are added, stirring for 2 days. The organic phase is washed with 100 ml of 0.5 N hydrochloric acid, then with 100 ml of a 3% solution of sodium bicarbonate and finally with 100 ml of water. The organic phase is dried over sodium sulfate and evaporated to dryness. The residue is treated with 250 ml of a 0.1 M NaOH aqueous solution at 5° C. for 3 hours, then the product is extracted with 4×250 ml of $CHCl_3$, the combined organic phases are dried over $Na_2SO_4$ and evaporated to dryness.

The residue is dissolved in 100 ml of methanol and adjusted to pH 2 with hydrochloric acid.

The hydrolysis of the orthoester is complete in about 30 minutes.

The mixture is evaporated to dryness under vacuum at room temperature and the residue is ground with diisopropyl ether, to obtain 0.5 g of crude epirubicin hydrochloride.

The purification is carried out according to Italian Patent n. 1,237,202, to yield pure epirubicin hydrochloride.

$^1$H-NMR (DMSO): ppm: 14.00 (s, 1H, phenol OH); 13.25 (s, 1H, phenol OH); 8.20–8.00 (broad, s, 3H, $NH_3^+$); 7.90 (m, 2H, H-1 and H-3); 7.65 (m, 1H, H-2) 5.80 (d, 1H, 4' OH); 5.55 (s, 1H, 9-OH); 5.30 (broad, s, 1H, H-1'); 4.95 (m, 2H, H-7 and 14-OH); 4.60 (m, 2H, 14-$CH_2$); 4.00 (broad s, 4H, $OCH_3$ and H-5'); 3.15 (m, 2H, H-3' and H-4'); 2.95 (q, 2H, 10H-$CH_2$); 2.30–1.70 (m, 4H, 8-$CH_2$ and 2'-$CH_2$); 1.25 (d, 3H, 5'-$CH_3$).

Example 16

A mixture of compound I ($R^1$=H) (5 g) in dichloromethane (500 ml) and pyridine (2.5 ml), cooled at 0° C., is slowly added with a solution of trifluoromethanesulfonic anhydride (2.5 ml) in dichloromethane (125 ml). The mixture is reacted for about 1 hour to obtain the triflate (compound II, $R^1$=H), then pyridine (6 ml) and triethylsilyl trifluoromethenesulfonate (15 ml) are added, warming at room temperature and stirring for 4 hours.

The tris silylate (compound III; $R^1$=H, T=$(C_2H_5)_3Si$) is added with a 0.1 M solution of triethylamine formate in dichloromethane (500 ml), stirring at room temperature for a further 15 hours.

The reaction mixture is washed with 500 ml of 0.25 N hydrochloric acid, then with a 2% solution of sodium bicarbonate and finally with 500 ml×2 of water. The organic phase is dried over sodium sulfate, filtered and evaporated to dryness.

5.2 g of compound IVf are obtained ($R^1$=H, R=H, R=Si$(CH_2CH_3)_3$, $R_3$=$CF_3CO$, $R_3$=$CF_3$ C).

$^1$H-NMR ($CDCl_3$): ppm: 13.96 (s, 1H, phenol OH); 13.39 (s, 1H, phenol OH); 8.14 (s, 1H, $HCO_2$); 8.02 (d, 1H, H-1); 7.77 (t, 1H, H-2); 7.36 (d, 1H, H-3); 6.39 (d, 1H, CONH); 5.41 (d, 1H, H-1'); 5.09 (m, 1H, H-7); 4.74 (t, 1H, H-4'); 4.51–4.31 (m, 2H, H-3' and H-5'); 4.07 (s, 3H, $OCH_3$); 3.43–3.00 (q, 2H, 10-$CH_2$); 2.31–1.64 (m, 2H, 8-$CH_2$ and 2'-$CH_2$); 2.29 (s, 3H, $COCH_3$) 1.29 (d, 3H, 5'-$CH_3$); 0.90 (t, 9H, Si$(CH_2\underline{CH}_3)_3$; 0.62 (q, 6H, Si$(\underline{CH}_2CH_3)_3$.

Example 17

Starting from IVf (5.2 g), with the same procedure as in example 6, 4.2 g of compound Vd are obtained.

Example 18

145 mg of n-trifluoroacetyladriamycin 14-valerate (0.2 mM) (AD32), obtained as described in U.S. Pat. No. 4,033,566, are dissolved in 10 ml of anhydrous $CH_2Cl_2$; the mixture is cooled at 5° C. and 48 μl of pyridine and 49 μl of triflic anhydride (0.3 mM) are added. After 2 hour cooling, when the reaction is completed, 49 μl (0.2 mM) of bis-trimethylsilylacetamide are added, heating at room temperature and stirring for 4 hours. The silylated product is added with 450 μl (3.3 mM) of triethylamine and 124 μl of formic acid (3.3 mM). The mixture is stirred at room temperature for a further 15 hours, then 2 ml of methanol and 2 ml of a 48% potassium fluoride aqueous solution are added. After two days, the phases are separated and the organic one is extracted with 10 ml of water. The organic phase is evaporated and the residue is crystallized from pure dichloromethane. The crystalline epiadriamycine 14-valerate-3-trifluoroacetamide has m.p. 230° C.; NMR (DMSO) and MS in agreement with the structure.

The recovered product has $R_f$ slightly lower than the starting compound AD32.

The hydrolysis of the product with a 0.05 M sodium hydroxide aqueous solution for 10 min. at 5° C. shows a partial formation of epirubicin, which is separated by chromatography and turns out to be the same as that already described.

Example 19

1 g of daunorubicin hydrochloride in 40 ml of anhydrous dichloromethane is reacted at room temperature with 0.4 ml of N-methylmorpholine and 0.6 g of FMOC chloride. After one hour, 3 ml of methanol are added leaving at room temperature for 12 hours. The reaction mixture is washed, extracted with 20 ml of 0.2 M HCl then with 20 ml of water, then it is dried over sodium sulfate and evaporated crystallizing the residue from diisopropyl ether. 0.5 g of a first crop are obtained, having melting point 174–175° C.

150 mg are reacted as in Example 18, but the final hydrolysis is carried out with 1 ml of dimethylformamide and 0.15 ml of diethylamine, instead of 0.05 M sodium hydroxide, for about 1 hour at −10° C. The reaction mixture is precipitated in 20 ml of ethyl ether and the obtained gum is filtered and suspended in water. 0.1 M Hydrochloric acid is added q.s. to dissolve the residue and to adjust pH to 3.7. The solution is purified on RP18, analogously to what described in Italian Pat. 1,237,202 obtaining pure epidaunorubicin which is the same as that already described in literature.

We claim:

1. A process for the preparation of epirubicin of formula (A)

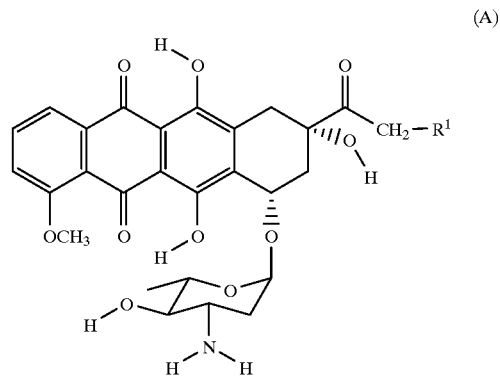

wherein $R^1$ is OH or $OCOR^2$, in which $R^2$ is a $C_1$–$C_4$-alkyl group, wherein the 4'-hydroxy group is equatorially oriented, which process comprises the steps of:

a) reacting N-protected daunorubicin of formula (I)

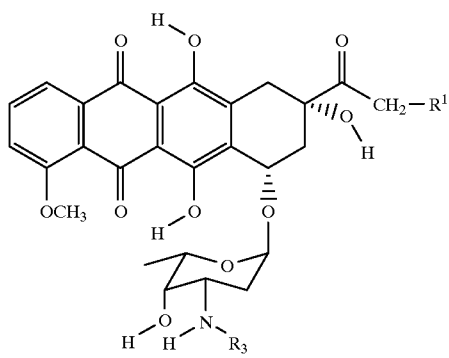

or a derivative thereof;
wherein $R^1$ is hydrogen, halogen; $R_3$ is an amino-protective group;
with triflic acid or a reactive derivative thereof, to give the compound of formula (II)

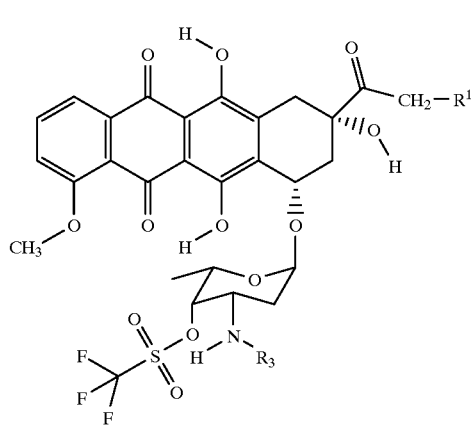

wherein $R^1$ and $R^3$ are as defined above;
b) protecting the hydroxy group at least at the 9-position, to give the intermediate of formula (III)

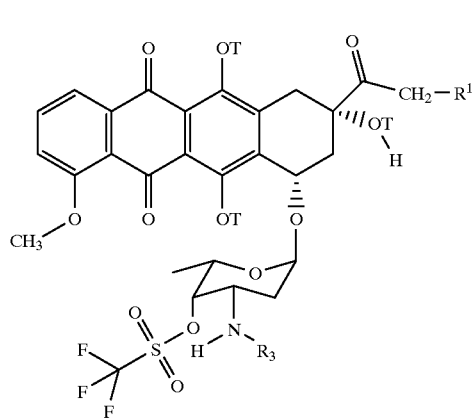

wherein T is a protective group, $R^1$ and $R^3$ are as defined above;
c) treating said compound III obtained in step b) with a salt of a secondary or tertiary amine with a carboxylic acid of formula RCOOH, wherein R is an aliphatic residue, or aromatic residue, to give the ester of formula (IV)

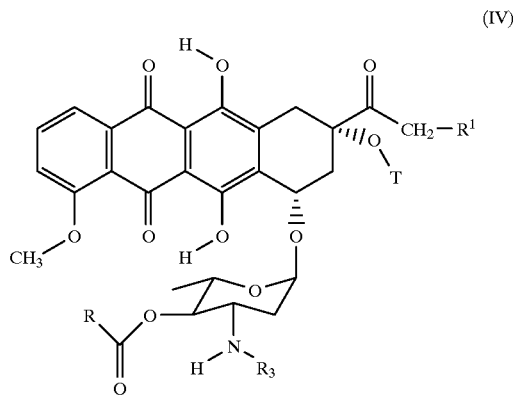

wherein R, $R^1$, $R^3$ and T are as defined above;
d) deprotecting said hydroxy group at the 9-position, to give the intermediate of formula (V)

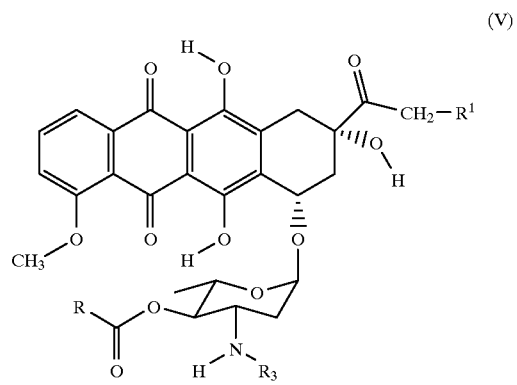

wherein R, $R^1$ and $R^3$ are as defined hereinabove;
e) hydrolyzing the ester from step d) to give N-protected epidaunorubicin of formula (VI)

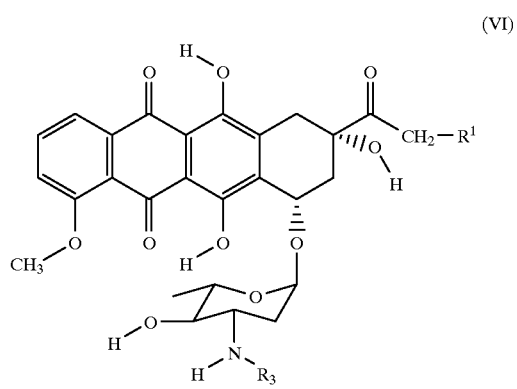

wherein $R^1$ and $R^3$ are as defined above;
f) removing said amino-protective group to obtain epidanorubicin wherein $R^1$ and $R^3$ are as defined hereinabove and
g) converting said epidaunorubicin into epirubicin of formula (A)

(A)

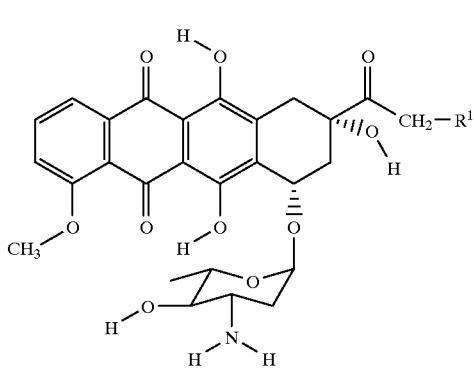

wherein $R^1$ is OH or $OCOR^2$, in which $R^2$ is as defined above.

2. The process according to claim 1 wherein in step b) in said carboxylic acid of formula RCOOH said aliphatic residue R is substituted or interrupted by hetero atoms or is a substituted or unsubstituted aromatic residue.

3. The process according to claim 1 wherein in said carboxylic acid salt in step c) is the triethylamine salt.

4. The process according to claim 2 wherein said acid is selected from the group consisting of formic, acetic, isobutyric, trimethylsilylacetic and p-nitrobenzoic acids.

5. The process according to claim 1 wherein step c) is effected at temperatures from 0° to 50° C.

6. The process according to claim 1 wherein the hydroxy groups at 6, 9 and 11 are protected with a trialkylsilyl group.

7. The process according to claim 1 wherein $R^3$ is trifluoroacetyl.

8. A process for the preparation of epirubicin of formula (A)

(A)

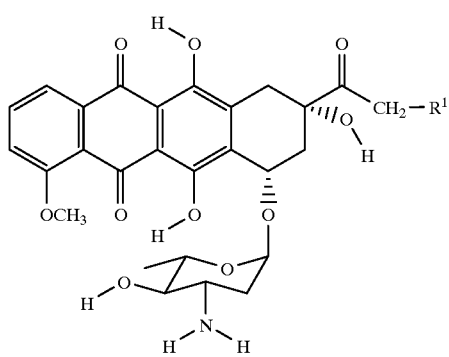

wherein $R^1$ is OH or $OCOR^2$, in which $R^2$ is a $C_1$–$C_4$ alkyl group, wherein the 4'-hydroxy group is equatorially oriented, which process comprises the steps of:

a) reacting N-protected daunorubicin derivative of formula (I)

(I)

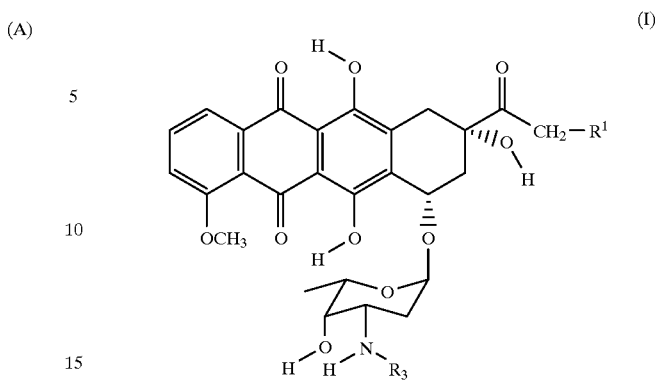

wherein $R^1$ is halogen, a protected hydroxy; $R^3$ is an amino-protective group;
with triflic acid or a reactive derivative thereof, to give the compound of formula (II)

(II)

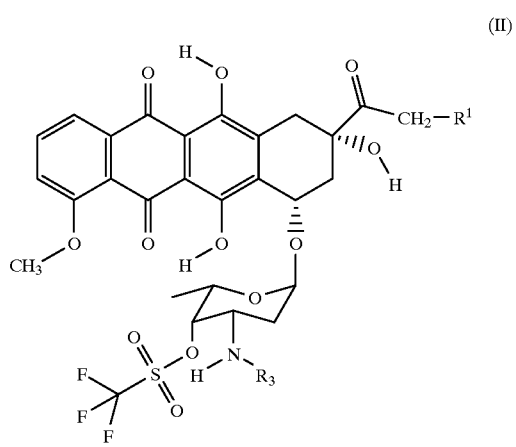

wherein $R^1$ and $R^3$ are as defined above;

b) protecting the hydroxy group at least at the 9-position, to give the intermediate of formula (III)

(III)

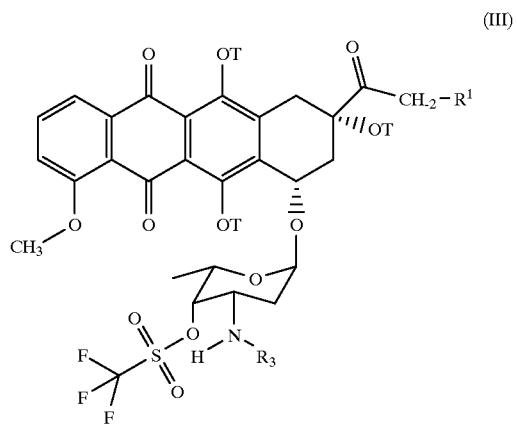

wherein T is a protective group, $R^1$ and $R^3$ are as defined above;

c) treating said compound III obtained in step b) with a salt of a secondary or tertiary amine with a carboxylic acid of formula RCOOH, wherein R is an aliphatic residue or aromatic residue, to give the ester of formula (IV)

(IV)

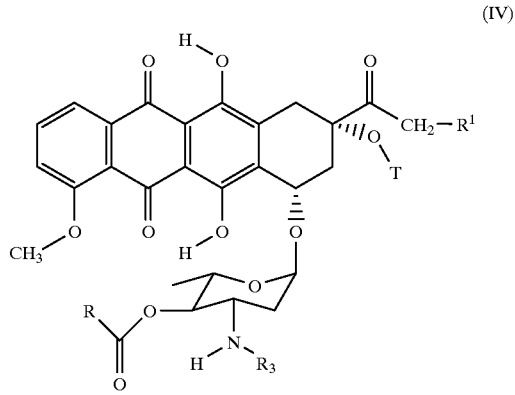

wherein R, $R^1$, $R^3$ and T are as defined above;

d) deprotecting said hydroxy group at the 9-position, to give the intermediate of formula (V)

(V)

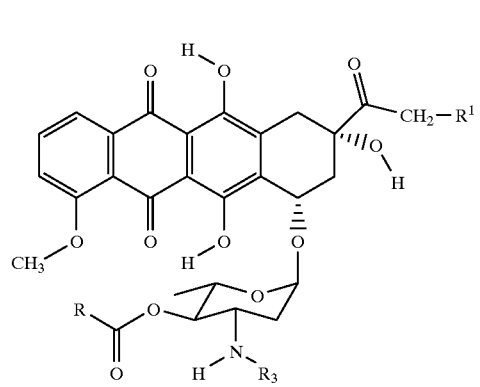

wherein R, $R^1$ and $R^3$ are as defined hereinabove;

e) hydrolyzing the ester from step d) to give N-protected epidaunorubicin derivative of formula (VI)

(VI)

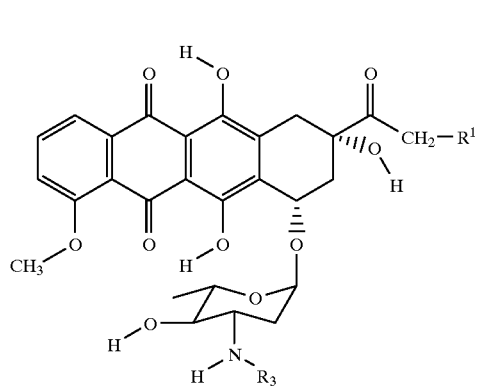

wherein $R^1$ and $R^3$ are as defined above;

f) removing said amino-protective group to obtain epirubicin of formula (A)

(A)

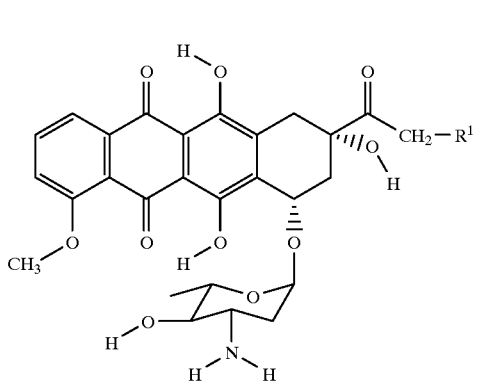

wherein $R^1$ is OH or $OCOR^2$, in which $R^2$ is as defined above.

9. The process according to claim 8 wherein in step b) in said carboxylic acid of formula RCOOH said aliphatic residue R is substituted or interrupted by hetero atoms or is a substituted or unsubstituted aromatic residue.

10. The process according to claim 8, wherein in said carboxylic acid salt in step c) is the triethylamine salt.

11. The process according to claim 9 wherein said acid is selected from the group consisting of formic, acetic, isobutyric, trimethylsilylacetic and p-nitrobenzoic acids.

12. The process according to claim 8 wherein step c) is effected at a temperature from 0° to 50° C.

13. The process according to claim 8 wherein the hydroxy groups at 6, 9 and 11 are protected with a trialkylsilyl group.

14. The process according to claim 8 wherein $R^3$ is trifluoroacetyl.

15. A process for the preparation of epirubicin of formula (A)

(A)

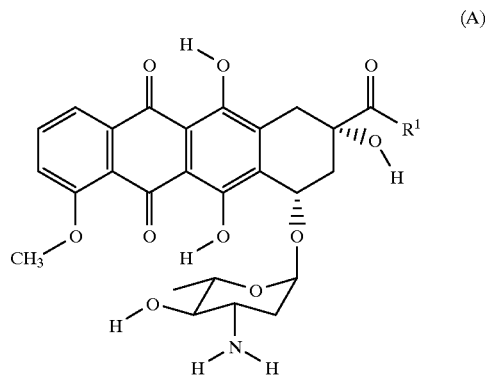

wherein $R^1$ is OH or $-OCOR^2$ in which $R^2$ is a $C_1$–$C_4$ alkyl group, wherein the 4'-hydroxy group is equatorially oriented, which comprises the following steps:

a) reacting doxorubicin of formula (C)

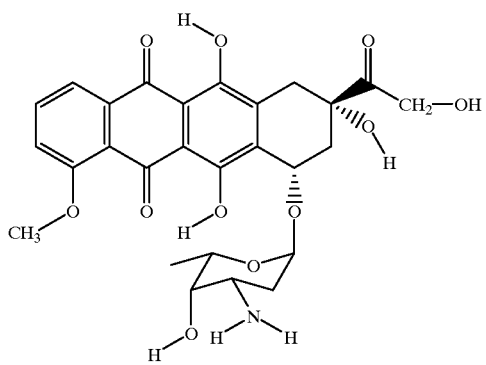

(C)

with a protective group for the hydroxy groups at the 9 and 14 positions and subsequently protecting the 3' amine with an amine-protecting group to give the compound of formula (VII)

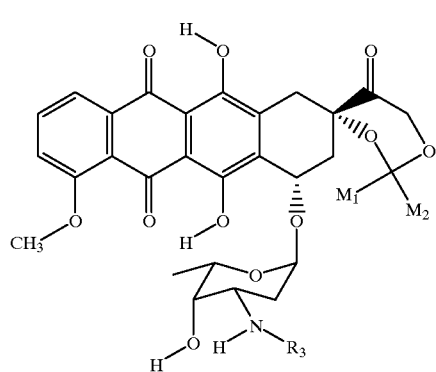

(VII)

wherein $M_1$ is a $C_1$–$C_4$ alkoxy group and $M_2$ is hydrogen or a $C_1$–$C_4$ alkyl group;

b) reacting said compound (VII) with triflic acid or a reactive derivative thereof, to give the compound of formula (VIII)

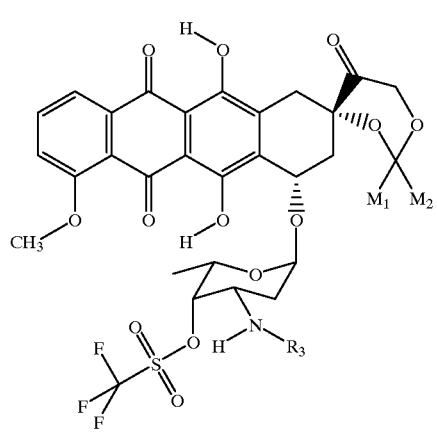

(VIII)

wherein $M_1$, $M_2$ and $R^3$ are as defined above;

c) protecting the hydroxy groups at the 6 and 11 positions to give the intermediate of formula (IX)

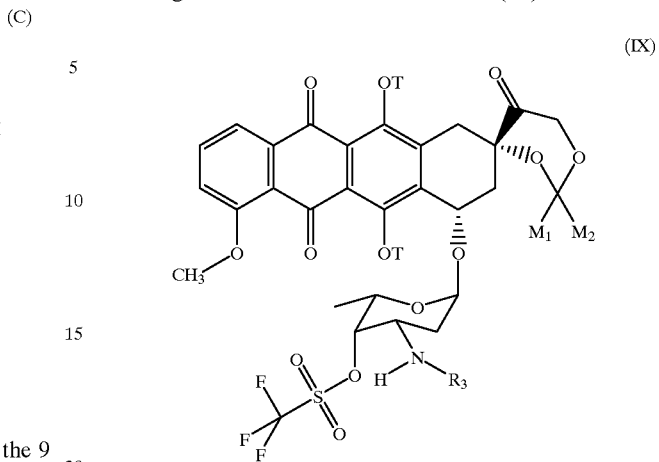

(IX)

wherein T is a protective group, $M_1$, $M_2$ and $R^3$ are as defined above;

d) reacting said compound (IX) obtained in step c) with a salt of a secondary or tertiary amine with a carboxylic acid of formula RCOOH wherein R is an aliphatic residue which is unsubstituted or is substituted or is interrupted by heteroatoms or an aromatic residue which is unsubstituted or substituted to give the ester of formula (X)

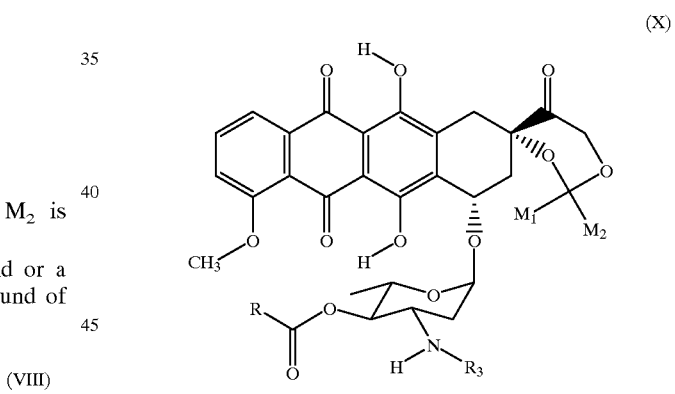

(X)

wherein R, $R^3$, $M_1$ and $M_2$ are as defined above;

e) hydrolyzing said ester and subsequently removing the protective group of said hydroxyl groups at 9 and 14 positions and the protective group of the amino group.

16. The process according to claim 15 wherein said carboxylic acid salt is the triethylamine salt.

17. The process according to claim 15 wherein the acid is selected from the group consisting of formic, acetic, isobutyric, trimethylsilylacetic and p-nitrobenzoic acids.

18. The process according to claim 15 wherein step d) is effected at a temperature ranging from 0° to 50° C.

19. The process according to claim 15 wherein $R^3$ is trifluoroacetyl.

20. A process for the preparation of epidaunorubicin of formula

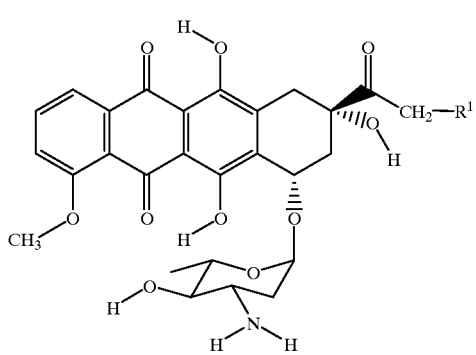

(A)

wherein $R^1$ is H, wherein the 4'-hydroxy group is equatorially oriented, which process comprises the steps of:

a) reacting N-protected daunorubicin of formula (I)

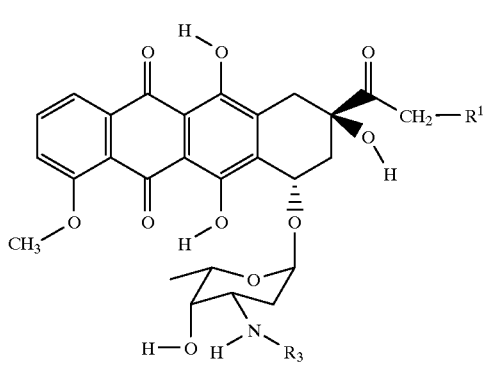

(I)

or a derivative thereof;
wherein $R^1$ is hydrogen, halogen, a protected hydroxy; $R^3$ is an amino-protective group;
with triflic acid or a reactive derivative thereof, to give the compound of formula (II)

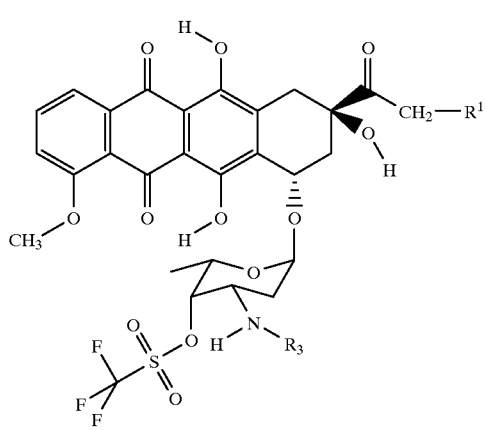

(II)

wherein $R^1$ and $R^3$ are as defined above;
b) protecting the hydroxy group at least at the 9-position, to give the intermediate of formula (III)

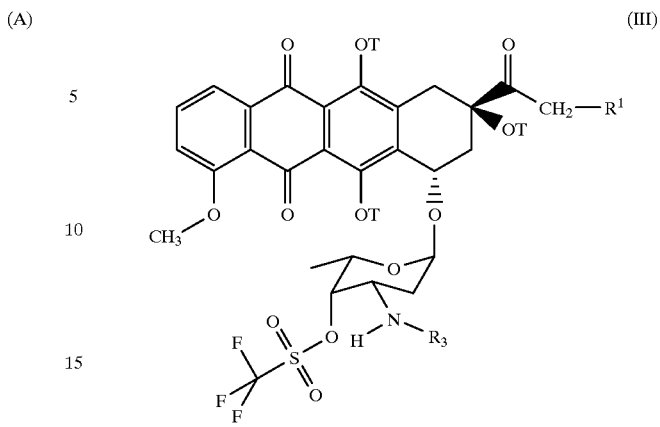

(III)

wherein T is a protective group, $R^1$ and $R^3$ are as defined above;

c) treating said compound III obtained in step b) with a salt of a secondary or tertiary amine with a carboxylic acid of formula RCOOH, wherein R is an aliphatic residue or aromatic residue, to give the ester of formula (IV)

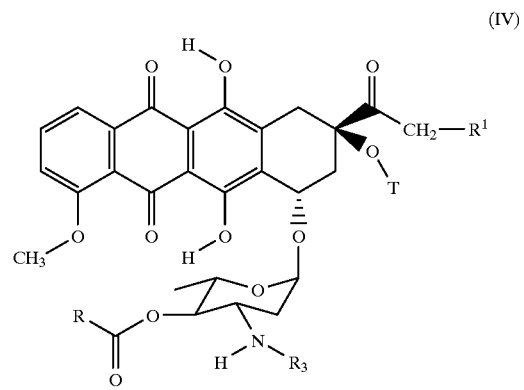

(IV)

wherein R, $R^1$, $R^3$ and T are as defined above;
d) deprotecting said hydroxy group at the 9-position, to give the intermediate of formula (V)

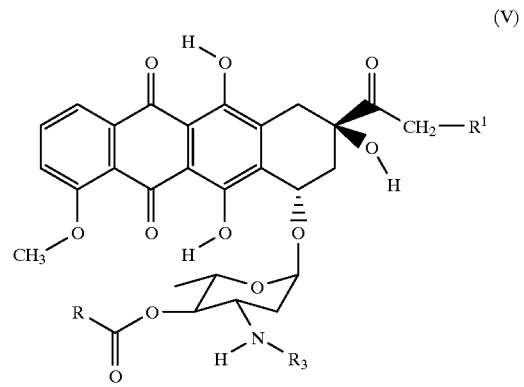

(V)

wherein R, $R^1$ and $R^3$ are as defined hereinabove;
e) hydrolyzing the ester from step d) to give N-protected epidaunorubicin of formula (VI)

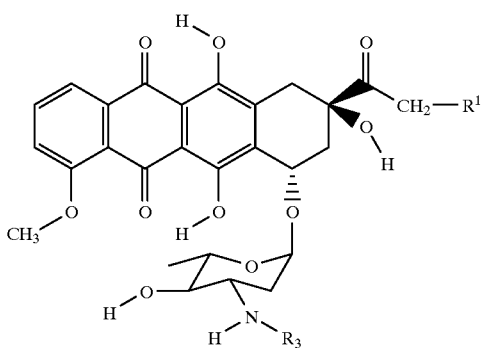

(VI)

wherein R¹ and R³ are as defined above;

f) removing said amino-protective group to obtain epi-danorubicin wherein R¹ and R³ are as defined hereinabove.

21. The process according to claim 20 wherein in step b) in said carboxylic acid of formula RCOOH said aliphatic residue R is substituted or interrupted by hetero atoms or is a substituted or unsubstituted aromatic residue.

22. The process according to claim 20 wherein said carboxylic acid salt in step c) is the triethylamine salt.

23. The process according to claims 20 wherein said acid is selected from the group consisting of formic, acetic, isobutyric, trimethylsilylacetic and p-nitrobenzoic acids.

24. The process according to claim 20 wherein step c) is effected at a temperature from 0° to 50° C.

25. The process according to claim 20 wherein the hydroxy groups at 6, 9 and 11 are protected with a trialkylsilyl group.

26. The process according to claim 20 wherein R³ is trifluoroacetyl.

* * * * *